United States Patent [19]
Jobard

[11] Patent Number: 5,443,837
[45] Date of Patent: Aug. 22, 1995

[54] ESTRUS SYNCHRONIZATION METHOD

[75] Inventor: Alain Jobard, Aulnay sous Bois, France

[73] Assignee: Roussel Uclaf, France

[21] Appl. No.: 136,458

[22] Filed: Oct. 13, 1993

[30] Foreign Application Priority Data

Oct. 13, 1992 [FR] France .................. 92 12220

[51] Int. Cl.$^6$ .................. A61F 2/02; A61K 31/58; A61K 31/585
[52] U.S. Cl. .................. 424/423; 514/173; 514/178; 514/179
[58] Field of Search ................ 424/423; 514/173, 178, 514/179

[56] References Cited

U.S. PATENT DOCUMENTS

| | | | |
|---|---|---|---|
| 3,257,278 | 6/1966 | Nomine | 514/178 |
| 3,478,067 | 11/1960 | Bertin et al. | 514/178 |
| 5,043,332 | 9/1991 | Teutsch et al. | 514/178 |

Primary Examiner—Thurman K. Page
Assistant Examiner—Carlos Azpuru
Attorney, Agent, or Firm—Bierman and Muserlian

[57] ABSTRACT

A method of synchronizing estrus in breeding animals comprising parenterally administering to breeding animals an estrus synchronizing amount of 17α-allyl-$\Delta^{4,9,11}$-estratriene-17β-ol-3-one.

7 Claims, No Drawings

ESTRUS SYNCHRONIZATION METHOD

STATE OF THE ART

Altrenogest or $17\alpha$-allyl-$\Delta^{4,9,11}$-estratriene-$17\beta$-ol-3-one is known for its progestogen properties (10th Edition of Merck Index, page 47, No. 309). Altrenogest is marketed as a veterinary medica- ment under the trademark Regumate ® with the following indications: for the synchronization of estrus in pubescent nullipa- rous sows and the incorporation of gilts in groups of multiparous sows after weaning piglets. It is recom- mended to administer to each of the animals to be treated 5 ml of a solution of 20 mg of altrenogest for 18 days, with the ingredients of a single meal. Up to now, altrenogest which has been the subject of numerous scientific publications has always been administered orally.

OBJECTS OF THE INVENTION

It is an object of the invention to provide an im- proved method of synchronizing estrus in breeding animals.

This and other objects and advantages of the inven- tion will become obvious from the following detailed description.

THE INVENTION

The novel method of the invention of synchronizing estrus in breeding animals comprises parenterally ad- ministering to breeding animals an estrus synchronizing amount of $17\alpha$-allyl-$\Delta^{4,9,11}$-estratriene-$17\beta$-ol-3-one. The administration method has the advantage of being both more certain and more precise than oral adminis- tration. There are less handling operations to carry out and one knows with precision what quantity of active ingredient each animal has received.

The results of the tests infra clearly show that excel- lent results are obtained with only 2 injections while the usual treatment requires 18 handling operations. The new use of the invention is therefore very profitable for the breeder from an economic point of view.

Examples of breeding are porcines, bovines and ovines, preferably, pubescent sows and more preferably nulliparous pubescent sows.

The preferred method of administration is intramus- cularly at a dose of 100 to 300 mg, preferably 200 mg of altrenogest.

The compositions may be in the form of ready-to-use solutions or suspensions or powders, preferably in the form of oily solutions with animal or vegetable oils.

The intramuscular administrations are preferably made twice at 5 to 10 day intervals at a dose of 0.5 to 2 mg/kg, more preferably 7 days apart. To be able to check on residues of the active ingredient and to be more precise, the animals are preferably tattooed be- hind the ear at which precise point the injections are administered.

In the following example, there is described a pre- ferred embodiment to illustrate the invention. How- ever, it is to be understood that the invention is not intended to be limited to the specific embodiment.

EXAMPLE

An oily solution was prepared consisting of 4 g of altrenogest, 10 ml of benzyl alcohol, 3 ml of ethanol and sufficient peanut oil for a total volume of 100 ml.

SYNCHRONIZATION METHOD

Pubescent nulliparous sows of Camborough stock approximately 9 months old were used and the sows were divided into 2 groups. Group I received altrenog- est in the form of Regumate ® in 500 g of food each morning for 18 days and the dose administered was 20 mg per day and per animal; Group II received two intramuscular injections of a 5 ml solution of 200 mg of altrenogest with injections at 7-day intervals. The sows were tattooed behind the ear so as to perform the two injections at a precise point. The animals, put under observation three months before the start of the treat- ment, were weighed at day D -5.

The animals of Group I were treated from D 1 to day D 18 and the animals of Group II received their two injections on day D4 and on day D11. Blood samples were taken regularly from the jugular vein for the plas- matic quantitative analysis of altrenogest. The sows were presented to boars twice a day from the onset of estrual manifestations and ultrasound scans were taken in the week D73→D 80. The animals were slaughtered 5 weeks after the scan and the genitalia of the sows were removed. The uterus and ovaries were inspected and the number of piglets per gestating sow was counted.

The injection zone was removed (10 cm diameter around the tattoo) to analyze altrenogest residues at the point of injection. The results obtained were as follows: in Group I, all the sows were covered between the 4th and 5th day after stopping the treatment and three sows in five were gestating with one sow having aborted. In Group II, five sows in six were covered between the 9th and 14th day after the second injection and four sows in five were gestating. No ovarian cystic development was discovered during the autopsy on the animals. The results can be summarized as follows:

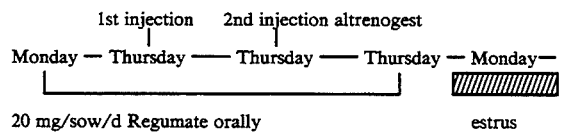

20 mg/sow/d Regumate orally      estrus

CONCLUSION

Altrenogest administered intramuscularly produced excellent results.

Various modifications of the method of the invention may be made without departing from the spirit or scope thereof and it is to be understood that the invention is intended to be limited only as defined in the appended claims.

What is claimed is:

1. A method of synchronizing estrus in breeding mammals comprising parenterally administering to breeding mammals an estrus synchronizing amount of $17\alpha$-allyl-$\Delta^{4,9,11}$-estratriene-$17\beta$-ol-3-one.

2. The method of claim 1 wherein the breeding mam- mals are pubescent sows.

3. The method of claim 1 wherein the breeding mam- mals are nulliparous pubescent sows.

4. The method of claim 1 wherein the administration is intramuscular at a dose of 100 to 300 mg.

5. The method of claim 1 wherein the administration is intramuscular twice at 5 to 10 day intervals.

6. The method of claim 5 wherein the interval is 7 days.

7. The method of claim 6 wherein the breeding mam- mal is a pubescent nulliparous sow.

* * * * *